United States Patent [19]

Adams

[11] 4,310,470

[45] Jan. 12, 1982

[54] PROCESS FOR PREPARING A DIALKYL PROPANEDIIMIDATE DIHYDROHALIDE

[75] Inventor: Charles D. Adams, Newark, Del.

[73] Assignee: E. I. Du Pont de Nemours and Company, Wilmington, Del.

[21] Appl. No.: 143,375

[22] Filed: Apr. 24, 1980

[51] Int. Cl.$^3$ .......................................... C07C 119/18
[52] U.S. Cl. ................................................. 260/453.7
[58] Field of Search ...................... 260/453 RW, 453.7

[56] References Cited

U.S. PATENT DOCUMENTS 3,256,309  6/1966  Gruber ......................... 260/453 RW
3,538,139  11/1970 Hagemeyer, Jr. ........... 260/453 RW
4,189,444  2/1980  Schuster et al. ............. 260/453 RW

OTHER PUBLICATIONS

Journal of the American Chemical Society, vol. 71, p. 43 (1949).

*Primary Examiner*—John M. Ford
*Assistant Examiner*—Robert C. Whittenbaugh

[57] ABSTRACT

An improved process for preparing a dialkyl propanediimidate dihydrohalide by reacting malononitrile, an alkyl alcohol, and hydrogen halide, wherein the improvement comprises conducting the reaction in an alkyl acetate as a solvent.

7 Claims, No Drawings

PROCESS FOR PREPARING A DIALKYL PROPANEDIIMIDATE DIHYDROHALIDE

BACKGROUND OF THE INVENTION

This invention relates to a process for preparing imido ester acid salts and, in particular, relates to an improvement in a process for preparing certain dialkyl propanediimidate dihydrohalides.

McElvain and Schroeder, JACS 71, 43 (1949), disclose the preparation of dimethyl and diethyl propanediimidate dihydrochloride by treating malononitrile and the corresponding alcohol with a large excess of hydrogen chloride using a chloroform-dioxane mixture and dioxane, respectively, as solvents. The process is disclosed to give high yields, but a reaction time of about 24 hours is required.

U.S. Pat. No. 3,402,193, issued on Sept. 17, 1968 to Hagemeyer, Jr. et al. discloses that in a process for the preparation of imido ester hydrochlorides by the reaction of a nitrile selected from the group consisting of alkyl, aralkyl and aryl nitriles having from 2 to 19 carbon atoms, a lower alkanol and hydrogen chloride at a temperature of $-10°$ to $50°$ C., improved results can be obtained by using in the reaction an excess of the nitrile of not less than 25% of the stiochiometric amount.

U.S. Pat. No. 3,538,139 which issued to Hagemeyer, Jr. et al. on Nov. 3, 1970 discloses that in the process for the preparation of imido ester hydrochlorides by the reaction of alkyl, aralkyl, aryl, alkaryl and aryloxyalkyl nitriles having from 2-19 carbon atoms with a lower alkanol and anhydrous hydrogen chloride at a temperature of $-10°$ to $50°$ C., improved results can be obtained by contacting the reactants while dissolved in an alkyl ester which has an alcohol moiety corresponding to the alcohol reactant and an acid moiety corresponding to the nitrile reactant.

Improvements in the process for preparing these imido ester hydrohalides are increasingly desirable and are constantly being sought. Furthermore, an improved process which provides both improved yields and shorter reaction times offers even greater attractions.

SUMMARY OF THE INVENTION

The present invention provides an improvement in a process for preparing a dialkyl propanediimidate dihydrohalide of the formula

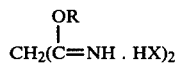

by reacting malononitrile, ROH and HX where R is methyl or ethyl and X is chloride or bromide. The improvement comprises conducting the reaction in an alkyl acetate of the formula CH₃COOR as a solvent at a temperature of from about $-5°$ C. to about $45°$ C. with ROH being present in an amount from stiochiometric to about 30% molar excess, the R group for the acetate being the same as that for ROH.

DETAILED DESCRIPTION OF THE INVENTION

In the improved process of the invention a dialkyl propanediimidate dihydrohalide of the formula

wherein
R is methyl or ethyl and
X is chloride or bromide
is prepared by reacting malononitrile, the appropriate alcohol selected from methyl or ethyl alcohol, and the appropriate anhydrous hydrogen halide. The reaction is conducted in either methyl or ethyl acetate, as a solvent, depending upon the alcohol being employed.

In the process of the invention, the alcohol is present in an amount from stiochiometric up to about a 30% molar excess with respect to the malononitrile. In preparing dimethyl propanediimidate dihydrochloride, which is a preferred embodiment of this invention, methanol is preferably present in a 10% molar excess with respect to the malononitrile.

The anhydrous hydrohalic acid is used in an excess in the improved process of the invention. Preferably, the acid is employed in an amount sufficient to saturate the solvent. In this manner, a relatively fast reaction rate will be provided.

In the process of the invention when methanol is a reactant, the solvent is methyl acetate and when ethanol is a reactant, the solvent is ethyl acetate. The solvent is used in an amount based on the amount of suspended solids. The weight ratio of solvent to suspended solids should not be less than about 2.5:1. The upper limit to solvent to solids ratio is not critical, but weight ratios of solvent to suspended solids in excess of about 10:1 become uneconomical.

In the process of the invention, the reaction is conducted at a temperature of about $-5°$ C. to about $45°$ C., preferably $10°-15°$ C. The pressure is preferably atmospheric, although greater than atmospheric pressures can be used. Reaction times vary from about 2-5 hours.

The invention will now be described in regards to the production of dimethyl propanediimidate, dihydrochloride which is a preferred embodiment; however, this description is not intended to limit the scope of the invention as previously or subsequently defined herein. Anhydrous hydrogen chloride is added to a solution of methanol in methyl acetate. Next, a solution of malononitrile in methyl acetate is added at a rate such that the temperature is maintained between $10°$ and $15°$ C. During the addition of malononitrile, the hydrogen chloride concentration is maintained as high as possible by passing more hydrogen chloride into the solution. As the reaction proceeds, a slurry results and is stirred for about 5 hours at $10°-15°$ C. Further, processing of the slurry gives the desired product.

The malononitrile can be added neat or as a methyl acetate solution to a methyl acetate solution of hydrogen chloride and methanol. It may also be added together with methanol to a solution of hydrogen chloride in methyl acetate.

In the comparison to prior art processes, in general, the process of the invention provides improved yields; shorter reaction times and higher concentration of product both of which permit greater efficiency in equipment use; and improved safety because the possibility of the product reacting exothermically with excess alcohol is reduced.

The invention is further illustrated by the following examples in which all temperatures are in degrees Centigrade and all percentages and parts are by weight unless otherwise specified.

EXAMPLE 1

PREPARATION OF DIMETHYL PROPANEDIIMIDATE DIHYDROCHLORIDE

Anhydrous hydrogen chloride gas (480 parts, 13.2 moles) is bubbled into a stirred solution of 280 parts (8.75 moles) of methanol in 1460 parts of methyl acetate in a 5-liter flask equipped with mechanical stirrer, thermometer, and connection to a water scrubber. A solution of 264 parts (4.0 moles) of malononitrile in 190 parts of methyl acetate is added over a 1-hour period at 10°–15°. Simultaneously, an additional 320 parts of anhydrous hydrogen chloride gas is bubbled into the flask over a 1.5-hour period at 10°–15°. There results a thick white slurry which is stirred at 13°–15° for 5 hours. The slurry is filtered to obtain a solid which is then washed thoroughly with methyl acetate and then dried in a vacuum oven at 25° overnight to yield 761 parts of a white solid as product. Based on malononitrile, the yield is 93.7%.

EXAMPLE 2

PREPARATION OF DIMETHYL PROPANEDIIMIDATE DIHYDROCHLORIDE

Anhydrous hydrogen chloride gas (75 parts) is sparged at a temperature of 18° into a solution of 8 parts (0.25 mole) of methanol in 194 parts of methyl acetate. A solution of 33 parts (0.50 mole) of malononitrile and 24 parts (0.75 mole) of methanol is added over a 25-minute period via a feed funnel. The feed funnel is rinsed with 4 parts (0.13 moles) of methanol. The hydrogen chloride gas sparging is resumed and continued for 40 minutes during which 30 parts of the gas are passed into the solution. There results a slurry which is stirred for 3.8 hours at 12°–14°, cooled to 5° and then filtered to provide a solid. This solid is washed with methyl acetate and dried to give 94.5 parts which corresponds to a 93.1% yield. Analysis for chloride gives 34.5% whereas the theoretical value is 34.9%.

We claim:

1. A process for preparing a dialkyl propanediimidate dihydrohalide of the formula

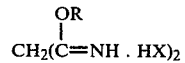

by reacting malononitrile, ROH and anhydrous HX wherein the improvement comprises conducting the reaction in an alkyl acetate of the formula $CH_3COOR$ as a solvent at a temperature of from about $-5°$ C. to about 45° C., said ROH being present in an amount from stoichiometric to about 30% molar excess and R being methyl or ethyl and X being chloride or bromide.

2. The process of claim 1 wherein R is methyl.
3. The process of claim 2 wherein X is chloride.
4. The process of claim 3 wherein the solvent is present in an amount equal to at least 2.5 times the weight of suspended solids.
5. The process of claim 4 wherein the temperature is from 10° C. to 15° C.
6. The process of claim 5 wherein the HCl is present in excess over the stoichiometric amount.
7. The process of claim 5 wherein $CH_3OH$ is present in a 10% molar excess over stoichiometric.

* * * * *